US012558436B2

(12) United States Patent (10) Patent No.: US 12,558,436 B2
Kim (45) Date of Patent: Feb. 24, 2026

(54) COMPOSITION AND METHOD FOR INHIBITING TAU PROTEIN ACCUMULATION, AGGREGATION, AND TANGLE FORMATION

(71) Applicant: INNOPEUTICS CORPORATION, Seoul (KR)

(72) Inventor: Tae Gyun Kim, Seoul (KR)

(73) Assignee: INNOPEUTICS CORPORATION, Seoul (KR)

( * ) Notice: Subject to any disclaimer, the term of this patent is extended or adjusted under 35 U.S.C. 154(b) by 281 days.

(21) Appl. No.: 17/284,145

(22) PCT Filed: Sep. 15, 2020

(86) PCT No.: PCT/KR2020/012429
§ 371 (c)(1),
(2) Date: Apr. 9, 2021

(87) PCT Pub. No.: WO2020/242279
PCT Pub. Date: Dec. 3, 2020

(65) Prior Publication Data
US 2022/0202955 A1 Jun. 30, 2022

(30) Foreign Application Priority Data

Sep. 19, 2019 (KR) ........................ 10-2019-0115466
Aug. 24, 2020 (KR) ........................ 10-2020-0106368

(51) Int. Cl.
| | |
|---|---|
| *A61K 48/00* | (2006.01) |
| *A61K 35/30* | (2015.01) |
| *A61K 38/17* | (2006.01) |
| *A61P 25/28* | (2006.01) |
| *C12N 15/86* | (2006.01) |

(52) U.S. Cl.
CPC ............ *A61K 48/005* (2013.01); *A61K 35/30* (2013.01); *A61K 38/177* (2013.01); *A61P 25/28* (2018.01); *C12N 15/86* (2013.01)

(58) Field of Classification Search
CPC .... A61K 48/005; A61K 35/30; A61K 38/177; A61P 25/28; C12N 15/86
See application file for complete search history.

(56) References Cited

U.S. PATENT DOCUMENTS

| | | | | |
|---|---|---|---|---|
| 10,555,972 B2 * | 2/2020 | Lee | .................... | A61K 38/1783 |
| 11,498,957 B2 * | 11/2022 | Lee | .................... | C07K 14/70567 |
| 2013/0052268 A1 | 2/2013 | Sangmi et al. | | |
| 2017/0354688 A1 * | 12/2017 | Lee | ................. | A61K 35/30 |

FOREIGN PATENT DOCUMENTS

| | | |
|---|---|---|
| KR | 20170101813 A | 9/2017 |
| KR | 10-1986366 B1 | 6/2019 |

OTHER PUBLICATIONS

Hareendran et al., "Adeno-associated virus (AAV) vectors in gene therapy: immune challenges and strategies to circumvent them" Rev. Med. Virol. (2013); 23: 399-413 (Year: 2013).*
Kinney et al., "Inflammation as a central mechanism in Alzheimer's disease" Alzheimer's & Dementia. (2018) 4: 575-590 (Year: 2018).*
Chu, et al., The Journal of Comparative Neurology (2006) 494: 495-514 (Year: 2006).*
Sleiman et al., Neuroscience Letters 457 (2009) p. 75-79 (Year: 2009).*
Moon et al., Aging Cell (2018) p. 1-11 (Year: 2018).*
Mudannayake, J., "Neuroprotective potential of AAV-mediated Nurr1 expression in a rat model of Parkinson's disease" a thesis submitted to The University of Auckland, 2015 (Year: 2015).*
Zhang, et al., Frontiers in Neurology (2018) 9(809): 1-7 (Year: 2018).*
Maiese, Kenneth J Transl Sci (2016) 2(4): 241-247 (Year: 2016).*
Benhelli-Mokrani, et al., Nucleic Acids Research (2018) 46(21): 11405-11422 (Year: 2018).*
Kim et al., Stem Cell Research (2016) 17: 534-543 (Year: 2016).*
Atkinson, Arthur Transl Clin Pharmacol (2017) 25(3): 117-124 (Year: 2017).*
Yi et al., Stem Cells and Regeneration (2014) 141(4): 761-772 (Year: 2014).*
Minho Moon, et al., Nurr1 (NR4A2) regulates Alzheimer's disease-related pathogenesis and cognitive function in the 5XFAD mouse model; Aging Cell / vol. 18, Issue 1, pp. 1-23: Dec. 4, 2018.
Sang-Min Oh, et al., Combined Nurr1 and Foxa2 roles in the therapy of Parkinson's disease; EMBIO Molecular Medicine, vol. 7, No. 5, pp. 510-525: May 2015.
Jin-il Kim, et al., The pharmacological stimulation of Nurri improves cognitive functions via enhancement of adult hippocampal neurogenesis, Stem Cell Research 17 (2016) 534-543.
Sang-Hoon Yi, et al., Foxa2 acts as a co-activator potentiating expression of the Nurr1-inducted DA phenotype via epigenetic regulation, The Company of Biologists Ltd. Development (2014) 141, 761-772.
Bloom et al., Amyloid-B and Tau: The Trigger and Bullet in Alzheimer Disease Pathogenesis, JAMA Neurology, vol. 71, No. 4, pp. 505-508, 2014.
Extended European Search Report dated Nov. 10, 2022 in European Application No. 20814122.6.
Ling H., Untangling the tauopathies: Current concepts of tau pathology and neurodegeneration, Parkinsonism and Related Disorders, vol. 46, pp. S34-S38, 2018.
Moon et al., Nurr1 (NR4A2) regulates Alzheimer's disease-related pathogenesis and cognitive function in the 5XFAD mouse model, Aging Cell, vol. 18, e12866, pp. 1-111, 2019.
Moon et al., Correlation between orphan nuclear receptor Nurr1 expressions and amyloid deposition in 5XFAD mice, an animal model of Alzheimer's disease, Journal of Neurochemistry, vol. 132, pp. 254-262, 2015.

(Continued)

*Primary Examiner* — Evelyn Y Pyla
*Assistant Examiner* — Katherine R Small
(74) *Attorney, Agent, or Firm* — KNOBBE, MARTENS, OLSON & BEAR, LLP

(57) ABSTRACT

Disclosed are a composition and method for inhibiting tau protein accumulation, aggregation, or tangle, the composition containing neurons or glia having Nurr1 and/or Foxa2 genes introduced thereinto, wherein the composition and method can be utilized in the prevention or treatment of a cerebral nervous disease caused by tau protein accumulation, aggregation, or tangle formation.

18 Claims, 11 Drawing Sheets

(56) References Cited

OTHER PUBLICATIONS

Office Action dated Oct. 16, 2022 in Korean Application No. KR 10-2020-0106368.

Song et al., Cografting astrocytes improves ell therapeutic outcomes in a Parkinson's Disease Model, The Journal of Clinical Investigation, vol. 128, No. 1, pp. 463-482, e93924, 2018.

Zhang et al., Tau Pathology in Parkinson's Disease, Frontiers in Neurology, vol. 9, Article 809, pp. 1-7, 2018.

Kovacs GG. Molecular Pathological Classification of Neurodegenerative Diseases: Turning towards Precision Medicine. Int J Mol Sci. Feb. 2, 2016;17(2):189. doi: 10.3390/ijms17020189.

Kovacs GG. Concepts and classification of neurodegenerative diseases. Handb Clin Neurol. 2017;145:301-307. doi: 10.1016/B978-0-12-802395-2.00021-3.

Jack CR Jr, Wiste HJ, Weigand SD, Therneau TM, Knopman DS, Lowe V, Vemuri P, Mielke MM, Roberts RO, Machulda MM, Senjem ML, Gunter JL, Rocca WA, Petersen RC. Age-specific and sex- specific prevalence of cerebral β-amyloidosis, tauopathy, and neurodegeneration in cognitively unimpaired individuals aged 50-95 years: a cross-sectional study. Lancet Neurol. Jun. 2017;16(6):435-444. doi: 10.1016/S1474-4422(17)30077-7.

Burnham SC, Coloma PM, Li QX, Collins S, Savage G, Laws S, Doecke J, Maruff P, Martins RN, Ames D, Rowe CC, Masters CL, Villemagne VL. Application of the NIA-AA Research Framework: Towards a Biological Definition of Alzheimer's Disease Using Cerebrospinal Fluid Biomarkers in the AIBL Study. J Prev Alzheimers Dis. 2019;6(4):248-255. doi: 10.14283/jpad.2019.25.

Zhu Y, Yao R, Li Y, Wu C, Heng L, Zhou M, Yan L, Deng Y, Zhang Z, Ping L, Wu Y, Wang S, Wang L. Protective Effect of Celecoxib on Early Postoperative Cognitive Dysfunction in Geriatric Patients. Front Neurol. Aug. 7, 2018;9:633. doi: 10.3389/fneur.2018.00633.

Kaizaki A, Tien LT, Pang Y, Cai Z, Tanaka S, Numazawa S, Bhatt AJ, Fan LW. Celecoxib reduces brain dopaminergic neuronaldysfunction, and improves sensorimotor behavioral performance in neonatal rats exposed to systemic lipopolysaccharide. J Neuroinflammation. Apr. 5, 2013;10:45. doi: 10.1186/1742- 2094-10-45.

Campolo M, Esposito E, Ahmad A, Di Paola R, Paterniti I, Cordaro M, Bruschetta G, Wallace JL, Cuzzocrea S. Hydrogen sulfide-releasing cyclooxygenase inhibitor ATB-346 enhances motor function and reduces cortical lesion vol. following traumatic brain injury in mice. J Neuroinflammation. Dec. 4, 2014;11:196. doi: 10.1186/s12974-014-0196-1.

Koulaeinejad N, Haddadi K, Ehteshami S, Shafizad M, Salehifar E, Emadian O, Ali Mohammadpour R, Ala S. Effects of Minocycline on Neurological Outcomes In Patients With Acute Traumatic Brain Injury: A Pilot Study. Iran J Pharm Res. 2019 Spring; 18(2):1086-1096. doi: 10.22037/ijpr.2019.1100677.

Hou Y, Xie G, Liu X, Li G, Jia C, Xu J, Wang B. Minocycline protects against lipopolysaccharide-induced cognitive impairment in mice. Psychopharmacology (Berl). Mar. 2016;233(5):905-16. doi: 10.1007/s00213-015-4169-6.

Alzheimer's Disease Anti-inflammatory Prevention Trial Research Group. Results of a follow-up study to the randomized Alzheimer's Disease Anti-inflammatory Prevention Trial (ADAPT). Alzheimers Dement. Nov. 2013;9(6):714-23. doi: 10.1016/j.jalz.2012.11.012.

Gyengesi E, Münch G. In search of an anti-inflammatory drug for Alzheimer disease. Nat Rev Neurol. Mar. 2020;16(3):131-132. doi: 10.1038/s41582-019-0307-9.

Rafii MS, Tuszynski MH, Thomas RG, Barba D, Brewer JB, Rissman RA, Siffert J, Aisen Ps; AAV2-NGF Study Team. Adeno-Associated Viral Vector (Serotype 2)-Nerve Growth Factor for Patients With Alzheimer Disease: A Randomized Clinical Trial. JAMA Neurol. Jul. 1, 2018;75(7):834-841. doi: 10.1001/jamaneurol. 2018.0233.

A double-blind placebo-controlled clinical trial of subcutaneous recombinant human ciliary neurotrophic factor (rHCNTF) in amyotrophic lateral sclerosis. ALS CNTF Treatment Study Group. Neurology. May 1996;46(5):1244-9. doi: 10.1212/wnl.46.5.1244.

A controlled trial of recombinant methionyl human BDNF in ALS: The BDNF Study Group (Phase III). Neurology. Apr. 22, 1999;52(7):1427-33. doi: 10.1212/wnl.52.7.1427.

Lang AE, Gill S, Patel NK, Lozano A, Nutt JG, Penn R, Brooks DJ, Hotton G, Moro E, Heywood P, Brodsky MA, Burchiel K, Kelly P, Dalvi A, Scott B, Stacy M, Turner D, Wooten VG, Elias WJ, Laws ER, Dhawan V, Stoessl AJ, Matcham J, Coffey RJ, Traub M. Randomized controlled trial of intraputamenal glial cell line-derived neurotrophic factor infusion in Parkinson disease. Ann Neurol. Mar. 2006;59(3):459-66. doi: 10.1002/ana.20737.

Marks WJ Jr, Bartus RT, Siffert J, Davis CS, Lozano A, Boulis N, Vitek J, Stacy M, Turner D, Verhagen L, Bakay R, Watts R, Guthrie B, Jankovic J, Simpson R, Tagliati M, Alterman R, Stern M, Baltuch G, Starr PA, Larson PS, Ostrem JL, Nutt J, Kieburtz K, Kordower JH, Olanow CW. Gene delivery of AAV2-neurturin for Parkinson's disease: a double-blind, randomised, controlled trial. Lancet Neurol. Dec. 2010;9(12):1164-1172. doi: 10.1016/S1474-4422(10)70254-4.

Shimura H, Schwartz D, Gygi SP, Kosik KS. CHIP-Hsc70 complex ubiquitinates phosphorylated tau and enhances cell survival. J Biol Chem. Feb. 6, 2004;279(6):4869-76. doi: 10.1074/jbc. M305838200.

Fath T, Eidenmüller J, Brandt R. Tau-mediated cytotoxicity in a pseudohyperphosphorylation model of Alzheimer's disease. J Neurosci. Nov. 15, 2002;22(22):9733-41. doi: 10.1523/JNEUROSCI.22-22-09733.2002.

Shimura H, Miura-Shimura Y, Kosik KS. Binding of tau to heat shock protein 27 leads to decreased concentration of hyperphosphorylated tau and enhanced cell survival. J Biol Chem. Apr. 23, 2004;279(17):17957-62. doi: 10.1074/jbc.M400351200.

Bandyopadhyay B, Li G, Yin H, Kuret J. Tau aggregation and toxicity in a cell culture model of tauopathy. J Biol Chem. Jun. 1, 2007;282(22):16454-64. doi: 10.1074/jbc.M700192200.

Zhao K, Ippolito G, Wang L, Price V, Kim MH, Cornwell G, Fulenchek S, Breen GA, Goux WJ, D'Mello SR. Neuron-selective toxicity of tau peptide in a cell culture model of neurodegenerative tauopathy: essential role for aggregation in neurotoxicity. J Neurosci Res. Nov. 15, 2010;88(15):3399-413. doi: 10.1002/jnr.22485.

Ji C, Sigurdsson EM. Current Status of Clinical Trials on Tau Immunotherapies. Drugs. Jul. 2021;81(10):1135-1152. doi: 10.1007/s40265-021-01546-6.

Bloom GS, Amyloid-β and Tau The Trigger and Bullet in Alzheimer Disease Pathogenesis, JAMA Neurol. 2014;71(4):505-508.

Guo et al., Modeling Alzheimer's Disease in Mouse without Mutant Protein Overexpression: Cooperative and Independent Effects of Aβ and Tau, PLOS ONE, vol. 8, Issue 11, e80706, 14 pages, 2013.

Oakley et al., Intraneuronal-Amyloid Aggregates, Neurodegeneration, and Neuron Loss in Transgenic Mice with Five Familial Alzheimer's Disease Mutations: Potential Factors in Amyloid Plaque Formation, The Journal of Neuroscience, vol. 26, No. 40, pp. 10129-10140, 2006.

Arendt et al., "Tau and tauopathies", Brain Res Bull, 126(Pt 3), pp. 238-292, Sep. 2016; Abstract only.

Götz et al., "Tau-targeted treatment strategies in Alzheimer's disease", British Journal of Pharmacology, vol. 165, pp. 1246-1259, 2012.

Metcalfe et al., "Relationship Between Tau Pathology and Neuroinflammation in Alzheimer's," Disease, Mount Sinai Journal of Medicine, vol. 77, pp. 50-58, 2010.

Wu et al., "Anti-neuroinflammatory effects of SLOH in Aβ-induced BV-2 microglial cells and 3xTg-AD mice involve the inhibition of GSK-3B," Neuroscience Letters, vol. 687, pp. 207-215, 2018.

Office Action issued in Korean Patent Application No. 10-2020-0106368 dated Aug. 16, 2022 in 20 pages.

Office Action issued in Korean Patent Application No. 10-2023-0081443 dated Oct. 12, 2023 in 8 pages.

Office Action issued in Canadian Patent Application No. 3,144,874 dated Jun. 29, 2023 in 5 pages.

Office Action issued in Chinese Patent Application No. 202080049749.9 dated Sep. 19, 2023 in 13 pages.

* cited by examiner

Water maze(18m+15m)

• Control (n=8), N+F (n=8)
• P-value was calculated by two sample T-test

Y maze(18m+15m)

· Control (n=8), N+F (n=8)
· P-value was calculated by two sample T-test

Control                    N+F

COMPOSITION AND METHOD FOR INHIBITING TAU PROTEIN ACCUMULATION, AGGREGATION, AND TANGLE FORMATION

BACKGROUND OF THE INVENTION

1. Field of the Invention

The present disclosure relates to a composition for inhibiting tau protein accumulation, aggregation, or tangle formation and, more particularly, to a technique for inhibiting tau protein accumulation, aggregation, or tangle formation by introducing Nurr1 and Foxa2 genes together or a Nurr1 gene alone to induce the expression of the genes.

2. Description of the Prior Art

Alzheimer's disease (AD) is a chronic neurodegenerative disease having symptoms most commonly including memory loss, difficulties with language, cognitive impairment, mood swings, etc.

Alzheimer's disease is neuropathologically characterized by the presence of plaques in brain cells, nervous tissues, vessels, and neurofibrillary tangles (NFTs) formed from the presence of tau protein accumulation. Alzheimer's disease is also characterized by the formation of amyloid β aggregations or plaques and the loss of synapses, etc. The cause for most Alzheimer's cases still remains unknown. Further, there has been no cure for Alzheimer's disease, thus far. Alzheimer's disease accounts for the most common cases of dementia, acting as a main cause of death, together with cardiovascular diseases and cancer. The frequency of Alzheimer's disease is predicted to increase with the average lifespan of humans.

In addition, an enormous expense is required for managing and treating patients with Alzheimer's disease, with the patients suffering from considerable mental anguish. Therefore, there is a need for effective method for preventing and treating patients suffering from Alzheimer's disease.

With respect to Alzheimer's disease, much research has recently been focused on tau protein. Indeed, the level of tau in cerebrospinal fluid increases at the prodromal stage of Alzheimer's disease, and the elevated level is stably maintained during the progression of the disease after its onset. NFT, which is a hyperphosphorylated tau protein, is found from the early stage of Alzheimer's disease and steadily increases in level with progression of the disease. That is, tau-mediated neuronal injury and dysfunction are pathologic findings in most patients suffering from Alzheimer's disease. NFT is also a biomarker of other tauopathies such as frontotemporal dementia (FTD), progressive supranuclear palsy (PSP), Pick's disease, chronic traumatic encephalopathy (CTE), etc. in addition to AD. Therapeutic products for those diseases have remained undeveloped thus far.

SUMMARY OF THE INVENTION

Leading to the present disclosure, the research conducted by the present inventors resulted in the experimental finding that the expression of the transcription factors Nurr1 and Foxa2 together, or Nurr1 alone, introduced in brain cells inhibited the accumulation, aggregation, or tangle of tau proteins. Particularly, when Nurr1 was expressed in combination with the coactivator Foxa2 the two genes were found to have a potent synergistic effect of inhibiting tau protein accumulation, aggregation, or tangle. In some embodiments, Nurr1 when expressed alone also was found to have substantial effects to inhibit tau protein.

Therefore, an aspect of the present disclosure is to provide a composition for inhibiting tau protein accumulation, aggregation, or tangle formation, the composition comprising a vector carrying Nurr1 and Foxa2 genes or the Nurr1 gene alone.

Another aspect of the present disclosure is to provide a composition for inhibiting tau protein accumulation, aggregation, or tangle, the composition comprising neurons or glia having Nurr1 and Foxa2 genes or a Nurr1 gene introduced thereinto.

Still another aspect of the present disclosure is to provide a composition for inhibiting tau protein phosphorylation, the composition comprising a vector carrying Nurr1 and Foxa2 genes or a Nurr1 gene.

Still another aspect of the present disclosure is to provide a composition for inhibiting tau protein phosphorylation, the composition comprising neurons or glia having Nurr1 and Foxa2 genes or a Nurr1 gene introduced thereinto.

Still another aspect of the present disclosure is to provide a composition for prevention or treatment of a disease caused by tau protein accumulation, aggregation, or tangle formation, the composition comprising a vector carrying Nurr1 and Foxa2 genes or a Nurr1 gene.

Still another aspect of the present disclosure is to provide a composition for prevention or treatment of a disease caused by tau protein accumulation, aggregation, or tangle, the composition comprising neurons or glia having Nurr1 and Foxa2 genes or a Nurr1 gene introduced thereinto.

Still another aspect of the present disclosure is to provide a composition for prevention or treatment of tauopathy, the composition comprising a vector carrying Nurr1 and Foxa2 genes or a Nurr1 gene.

Still another aspect of the present disclosure is to provide a composition for prevention or treatment of tauopathy, the composition comprising neurons or glia having Nurr1 and Foxa2 genes or a Nurr1 gene introduced thereinto.

The present inventors have performed research efforts relating to methods for inhibiting accumulation, aggregation, or tangle formation of tau protein, which is known as a main cause of tauopathy. As a result, the present inventors have discovered that introduction of Nurr1 and Foxa2 genes together or a Nurr1 gene alone, followed by expression of the genes had effects of inhibiting tau protein accumulation, aggregation, or Neurofibrillary tangle(NFL) formation and tau protein phosphorylation.

In accordance with an aspect of the present disclosure, there is provided a composition for inhibiting tau protein accumulation, aggregation, or tangle formation, the composition comprising a vector carrying Nurr1 and Foxa2 genes.

In accordance with another aspect of the present disclosure, there is provided a composition for inhibiting tau protein accumulation, aggregation, or tangle formation, the composition comprising a vector carrying a Nurr1 gene and not the Foxa2 gene.

In accordance with still another aspect of the present disclosure, there is provided a composition for inhibiting tau protein accumulation, aggregation, or tangle formation, the composition comprising neurons or glia having Nurr1 and Foxa2 genes introduced thereinto.

In accordance with still another aspect of the present disclosure, there is provided a composition for inhibiting tau protein accumulation, aggregation, or tangle formation, the composition comprising neurons or glia having a Nurr1 gene introduced thereinto.

In accordance with still another aspect of the present disclosure, there is provided a composition for inhibiting tau protein phosphorylation, the composition comprising a vector carrying Nurr1 and Foxa2 genes.

In accordance with still another aspect of the present disclosure, there is provided a composition for inhibiting tau protein phosphorylation, the composition comprising a vector carrying a Nurr1 gene.

In accordance with still another aspect of the present disclosure, there is provided a composition for inhibiting tau protein phosphorylation, the composition comprising neurons or glia having Nurr1 and Foxa2 genes introduced thereinto.

In accordance with still another aspect of the present disclosure, there is provided a composition for inhibiting tau protein phosphorylation, the composition comprising neurons or glia having a Nurr1 gene introduced thereinto.

In accordance with still another aspect of the present disclosure, there is provided a composition for prevention or treatment of a disease caused by tau protein accumulation, aggregation, or tangle formation, the composition comprising a vector carrying Nurr1 and Foxa2 genes.

In accordance with still another aspect of the present disclosure, there is provided a composition for prevention or treatment of a disease caused by tau protein accumulation, aggregation, or tangle formation, the composition comprising a vector carrying a Nurr1 gene.

In accordance with still another aspect of the present disclosure, there is provided a composition for prevention or treatment of a disease caused by tau protein accumulation, aggregation, or tangle formation, the composition comprising neurons or glia having Nurr1 and Foxa2 genes introduced thereinto.

In accordance with still another aspect of the present disclosure, there is provided a composition for prevention or treatment of a disease caused by tau protein accumulation, aggregation, or tangle formation, the composition comprising neurons or glia having a Nurr1 gene introduced thereinto.

In accordance with still another aspect of the present disclosure, there is provided a pharmaceutical composition for prevention or treatment of tauopathy, the pharmaceutical composition comprising a vector carrying Nurr1 and Foxa2 genes.

In accordance with still another aspect of the present disclosure, there is provided a pharmaceutical composition for prevention or treatment of tauopathy, the pharmaceutical composition comprising a vector carrying a Nurr1 gene.

In accordance with still another aspect of the present disclosure, there is provided a pharmaceutical composition for prevention or treatment of tauopathy, the pharmaceutical composition comprising neurons or glia having Nurr1 and Foxa2 genes introduced thereinto.

In accordance with still another aspect of the present disclosure, there is provided a pharmaceutical composition for prevention or treatment of tauopathy, the pharmaceutical composition comprising a vector carrying a Nurr1 gene.

According to an embodiment of the present disclosure, the tauopathy is a disease selected from the group consisting of tau-positive Alzheimer's disease, dementia with Lewy bodies, frontotemporal dementia (FTD), multi-Infarct dementia (MID), frontotemporal lobar degeneration (FTLD), progressive cupranuclear palsy (PSP), Pick's disease, chronic traumatic encephalopathy (CTE), corticobasal degeneration (CBD), globular glial tauopathy, Huntington's disease, ganglioglioma, gangliocytoma, primary age-related tauopathy (PART), argyrophilic grain disease, lead encephalopathy, lipofuscinosis, Lytico-Bodig disease, and meningioangiomatosis, but is not limited thereto.

In the present disclosure, the Foxa2 gene together with the Nurr1 gene can be used in the prevention and treatment of Alzheimer's disease, which is a type of tauopathy. The expression through the introduction of Nurr1 and Foxa2 or the introduction of Nurr1 alone was found to alleviate pathological symptoms of Alzheimer's disease. The pathological symptoms may include (1) tau protein accumulation, 2) beta-amyloid accumulation, 3) brain cell aging, 4) synapse loss; and 5) accumulation of peripheral immune cells. In addition, the expression of Nurr1 and Fox2 together or the expression of Nurr1 alone led to neurotrophication of brain cells and thus showed the effects of preventing and treating Alzheimer's disease, which is a kind of tauopathy.

In one embodiment of a method of the present disclosure, the expression "introducing (transducing) Nurr1 and Foxa2" refers to introducing nucleic acids encoding the two genes together into brain cells. The two genes may be separately or simultaneously introduced.

In the method of the present disclosure, the expression "introducing (transducing) Nurr1" refers to introducing a nucleic acid encoding the Nurr1 gene into brain cells.

To introduce genes encoding Nurr1 and/or Foxa2 into brain cells, technical methods of introducing a gene into cells, which are well known in the art, may be used, for example, a DNA-calcium precipitation assay, a method using liposomes, a method using polyamines, an electroporation assay, a method using a retrovirus, a method using an adenovirus, a method using an adeno-associated virus (AAV), and the like.

Viral or non-viral vectors may be used when carrying Nurr1 and/or Foxa2. Examples of viral vectors include adeno-associated viruses (AAV), adenoviruses, retroviruses, and/or lentiviruses. Examples of non-viral vectors include RNA molecules, plasmids, liposome complexes, molecular conjugates, and/or gene scissor proteins (CRISPR, e.g., Cas9). Therefore, the introduction of Nurr1 and/or Foxa2 according to the present disclosure encompasses, as an embodiment, inserting nucleic acids encoding Nurr1 and Foxa2 into different expression vectors or one expression vector and then introducing the expression vector(s) into brain cells.

In some embodiments of expressing Nurr1 and/or Foxa2, gene editing techniques may be used. The gene editing techniques are used to show a target genetic trait by freely correcting genetic information of a living organism. Examples of a system that can be used in genetic editing techniques include zinc finger nuclease (ZFN), transcription activator-like effector nuclease (TALEN), and clustered regularly interspaced short palindromic repeats/CRISPR-associated protein 9 (CRISPR/Cas 9).

As used herein, the term "RNA-guided nuclease" refers to a nuclease that can recognize and cleave a particular position on a target genome, and especially, refers to a nuclease having target specificity by guided RNA. The RNA-guided nuclease may be, but is not limited to, specifically, Cas protein derived from the microbial immune system CRISPR and, more specifically, the RNA-guided nuclease may include CRISPR-associated protein 9 (Cas9) nuclease and a variant thereof, Cas9 nickase.

As used herein, the term "Cas protein" is a main protein component of the CRISPR/Cas system and is a protein that can act as an activated endonuclease. The Cas protein can form a complex together with CRISPR RNA (crRNA) and trans-activating crRNA (tracrRNA) to exhibit activity thereof.

The Cas9 nuclease recognizes a specific nucleotide sequence in the genome of animal and plant cells, including human cells, to thereby cause a double strand break (DSB). The double strand break encompasses cleaving the double strand of DNA to make a blunt end or a cohesive end. DSBs are efficiently repaired by the homologous recombination or non-homologous end-joining (NHEJ) mechanism in cells, and in this procedure, a desired mutation can be introduced into a target site by a researcher. The RNA-guided nuclease may an artificially or engineered non-naturally occurring RNA-guided nuclease.

The Cas9 nickase may include one or more mutations in one of its catalytic domains, wherein the one or more mutations are selected from the group consisting of D10A, E762A, and D986A in the RuvC domain or the one or more mutations are selected from the group consisting of H840A, N854A, and N863A in the HNH domain. The Cas9 nickase causes a single strand break unlike Cas9 nuclease. Therefore, two guided-RNAs are used which allow the Cas9 nickase to work, and function as a pair. The two guided-RNAs direct sequence-specific binding of the CRISPR complex to each target sequence, and direct the cleavage of one strand of the DNA duplex near each target sequence to induce two nicks in different DNA strands.

The Cas protein, or gene information, can be obtained from a known database, such as GenBank of National Center for Biotechnology Information (NCBI). Specifically, the Cas protein may be Cas9 protein. In addition, the Cas protein may be, but is not limited to, Cas protein derived from the genus *Staphylococcus*, the genus *Streptococcus*, the genus *Neisseria*, the genus *Pasteurella*, the genus *Francisella*, or the genus *Campylobacter*, and more specifically, Cas9 protein of the genus *Staphylococcus*. However, the present disclosure is not limited to the above-described examples. In the present disclosure, the Cas protein may be a recombinant protein.

The nucleic acids encoding Nurr1 and/or Foxa2 may be used without limitation as long as the nucleic acids have nucleotide sequences encoding Nurr1 and/or Foxa2, as known in the art. Also, the nucleic acids may have nucleotide sequences encoding respective functional equivalents of Nurr1 and/or Foxa2. A functional equivalent refers to a polypeptide having a sequence homology (or identity) of at least 60%, preferably at least 70%, more preferably at least 80% to amino acid sequences of Nurr1 and/or Foxa2. For example, the functional equivalent may include a polypeptide having a sequence homology of 60%, 61%, 62%, 63%, 64%, 65%, 66%, 67%, 68%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. The functional equivalent may be generated as a result of addition, substitution, or deletion of a part of each of the amino acid sequences. The deletion or substitution of amino acids is preferably located at a region that is not directly associated with the physiological activity of the polypeptide of the present disclosure.

In addition, nucleic acids encoding Nurr1 and/or Foxa2 protein may be prepared using a genetic recombinant method known in the art. Examples of the genetic recombinant methods include PCR amplification for amplifying nucleic acids from a genome, chemical synthesis, or a technique of preparing a cDNA sequence.

The nucleic acids encoding Nurr1 and/or Foxa2 are operably linked to an expression control sequence and thus can be inserted into an expression vector. The term "operably linked" means that one nucleic acid fragment is linked to another nucleic acid fragment so that the function or expression of the one nucleic acid fragment is affected by the another nucleic acids fragment. In addition, the term "expression control sequence" means a DNA sequence that controls the expression of an operably linked nucleic acid sequence in a particular host cell. Such a control sequence includes a promoter for initiating transcription, any operator sequence for controlling transcription, a sequence for encoding a suitable mRNA ribosomal binding site, and a sequence for controlling the termination of transcription and translation. All of these sequences may be generally expressed as "DNA construct including nucleic acids encoding Nurr1 and/or Foxa2".

The term "expression vector" refers to a plasmid, a viral vector, or other mediators into which nucleic acids encoding structural genes may be inserted and in which the nucleic acids may be expressed in host cells, as known in the art. In one embodiment, the expression vector may be a viral vector. Examples of viral vectors includes, but is not limited to, adenoviral vectors, adeno-associated viral (AAV) vectors, herpes viral vectors, avipox viral vectors, lentiviral vectors, and the like. Especially, methods using adeno-associated virus (AAV) or lentivirus are preferable.

The adeno-associated viral (AAV) vectors are constructed by introducing materials capable of making a virus into particular cells, and the lentiviral vectors are constructed through several steps so that viruses can be produced in a particular cell line. The main advantages of adeno-associated viral (AAV) or lentiviral vectors for gene therapy are efficiency and stability.

An expression vector containing the nucleic acids according to the present disclosure may be introduced into brain cells by a method known in the art, for example, but not limited to, transient transfection, microinjection, transduction, cell fusion, calcium phosphate precipitation, liposome-mediated transfection, DEAE dextran-mediated transfection, polybrene-mediated transfection, electroporation, gene gun, and other known methods used to introduce the nucleic acids into cells. For example, Nurr1 and/or Foxa2 genes may be inserted into the AAV or lentiviral vector to construct an expression vector, and this vector is then transduced into packaging cells. The transduced packaging cells are incubated and then filtered to obtain an AAV or lentiviral solution, and this solution is used to infect brain cells, neurons, and/or neural progenitor cells, thereby introducing the Nurr1 and/or Foxa2 genes into brain cells. Subsequently, after confirming that Nurr1 and/or Foxa2 are alone or simultaneously expressed using a selective marker included in the AAV or lentiviral vector, desired brain cells can be obtained.

According to an embodiment, brain cells having Nurr1 and Foxa2 genes introduced and expressed therein may be prepared by a method comprising the following steps:

(a) constructing a recombinant viral vector containing a DNA construct harboring nucleic acids encoding Nurr1 and Foxa2;

(b) transfecting a virus-producing cell line with the recombinant viral vector to prepare a Nurr1- and Foxa2-expressed recombinant virus; and (c) infecting brain cells with the Nurr1- and Foxa2-expressed recombinant virus.

First, a DNA construct harboring the nucleic acids encoding Nurr1 and Foxa2 is prepared as described above.

According to an embodiment, brain cells having Nurr1 introduced and expressed therein may be prepared by a method comprising the following steps:

(a) constructing a recombinant viral vector containing a DNA construct harboring a nucleic acid encoding Nurr1;

(b) transfecting a virus-producing cell line with the recombinant viral vector to prepare a Nurr1-expressed recombinant virus; and (c) infecting brain cells with the Nurr1-expressed recombinant virus.

A DNA construct harboring the nucleic acid encoding Nurr1 and/or Foxa2 may also be prepared as described above.

The DNA construct may be operably linked to an expression control sequence, for example, a promoter, and inserted to a viral vector known in the art, thereby constructing a recombinant viral vector. Thereafter, the recombinant viral vector harboring the nucleic acids encoding Nurr1 and/or Foxa2 is introduced into a virus-producing cell line, thereby preparing a recombinant virus expressing Nurr1 and/or Foxa2. A cell line producing a virus corresponding to the viral vector used may be used as the virus-producing cell line. Then, brain cells are infected with the recombinant AAV or lentivirus expressing Nurr1 and Foxa2 or Nurr1. This may be carried out by using any methods known in the art.

The brain cells expressing Nurr1 and/or Foxa2 proteins according to the present disclosure may proliferate and be incubated by any method known in the art.

The brain cells of the present disclosure are incubated in a culture broth that helps the survival or proliferation of a desired type of brain cell. A culture broth often nourished with free amino acids instead of a serum is preferably used. The culture broth is preferably supplemented with an additive developed to continuously incubate the brain cells. Examples of the additive include an N2 medium and a B27 additive, which are commercially available from Gibco, bovine serum, and the like. During incubation, the medium is preferably exchanged with fresh medium while the conditions of the medium and cells are observed. In this case, the brain cells may be subcultured when the brain cells continuously proliferate into confluence to form neurospheres. The subculture may be carried out every approximately 7 to 8 days, depending on the particular protocol and observed growth characteristics of the cells.

As described herein, the introduction and expression of Nurr1 and/or Foxa2 in the brain cells alleviates pathological symptoms of Alzheimer's disease, which is a kind of tauopathy, such as (1) beta-amyloid accumulation, (2) tau protein accumulation, (3) brain cell aging, (4) synapse loss; and (5) accumulation of peripheral immune cells, and leads to neurotrophication of brain cells and thus help prevent and treat Alzheimer's disease, which is a kind of tauopathy. The expression of Nurr1 and Foxa2 or Nurr1 alleviates pathological symptoms of Alzheimer's disease, which is a kind of tauopathy, and shows effects of preventing and treating Alzheimer's disease, which is a kind of tauopathy.

In another aspect, the present disclosure provides use of brain cells having Nurr1 and Foxa2 introduced thereinto for treatment of tauopathy.

Furthermore, the present disclosure provides use of brain cells having Nurr1 introduced thereinto for treatment of tauopathy.

For example, these cells may be therapeutically used by directly introducing the brain cells having Nurr1 and Foxa2 or Nurr1 introduced thereinto into the substantia nigra site depending on the disease or condition to be treated. In addition, the brain cells having Nurr1 and Foxa2 or Nurr1 introduced thereinto can be therapeutically used by administration or transplantation in the form of a composition containing a therapeutically effective amount thereof. The present disclosure also includes a method for treatment of tauopathy.

An aspect of the present disclosure relates to a composition, gene therapeutic agent, or cell therapeutic agent, containing brain cells having Foxa2 and Nurr1 or Nurr1 introduced thereinto as an active ingredient, for prevention or treatment of a disease (e.g., Alzheimer's disease) caused by tau protein accumulation, aggregation, or NFL.

The gene therapeutic agent or cell therapeutic of the present disclosure prevents the accumulation of tau protein and/or beta-amyloid and protects brain cells including neurons and glia from damage, thereby allowing memory-related neurons to be supplemented (regenerated) or again constructed (restored).

The term "regeneration" refers to the supplementation of a lost part of a formed organ or an individual, and the term "restoration", which may be called "reconstitution", refers to reconstruction of a tissue, and again reconstruction of a tissue or organ from cells or tissues that have been dissociated once.

The composition or cell therapeutic agent of the present disclosure may be prepared into an appropriate preparation by containing an acceptable carrier depending on the administration mode. Preparations suitable for different administration modes are known, and may include preparations that typically pass through a membrane and facilitate migration.

In addition, the composition of the present disclosure may be used in the form of a general medicinal preparation. A parenteral preparation may be prepared in the form of a sterile aqueous solution, a non-aqueous solvent, a suspending agent, an emulsion, or a freeze-drying agent. For oral administration, the composition of the present disclosure may be prepared in the form of a tablet, troche, capsule, elixir, suspension, syrup, or wafer. For injections, the composition may be prepared into a single-dose ampoule or multi-dose container. In addition, the composition for treatment of the present disclosure may be administered together with a pharmaceutically acceptable carrier. For example, for oral administration, a binder, a lubricant, a disintegrator, an excipient, a solubilizer, a dispersing agent, a stabilizer, a suspending agent, a coloring agent, a perfume, or the like may be used. For injections, a buffer, a preservative, an analgesic, a solubilizer, an isotonic agent, a stabilizer, or the like may be used. For topical administration, a substrate, an excipient, a lubricant, a preservative, or the like may be used.

In addition, a method for treating tauopathy by using the composition for treatment of the present disclosure may include administering to a subject or patient through a general route in which a predetermined material is introduced, in an appropriate manner. Examples of the administration method include intracranial administration, intraventricular administration, spinal cavity administration, intraperitoneal administration, intravenous administration, intramuscular administration, subcutaneous administration, intradermal administration, oral administration, topical administration, intranasal administration, intrapulmonary administration, and rectal administration, but are not limited thereto. However, the oral composition may be digested in cells upon oral administration, and therefore, it is preferable that an active drug is coated or the oral composition is formulated to protect degradation in the stomach.

The pharmaceutical composition may also be administered by any device that can deliver an active material to a target cell. Preferable administration modes and preparations include a hippocampus injection using the stereotactic system, an intraventricular injection, the cerebrospinal fluid injection, intravenous injection, a subcutaneous injection, an intradermal injection, an intramuscular injection, or a drop injection. The injections may be prepared by using an aqueous solvent, such as physiological saline solution or Ringer's solution, and a non-aqueous solvent, such as vegetable oil, a higher fatty acid ester (e.g., ethyl oleate), an alcohol (e.g., ethanol, benzyl alcohol, propylene glycol, or glycerin). The injections may contain a pharmaceutical carrier, such as a stabilizer for deterioration prevention (e.g., ascorbic acid, sodium hydrogen sulfite, sodium pyrolacto-sulfate, BHA, tocopherol, EDTA, etc.), an emulsifier, a buffer for pH adjustment, a preservative for inhibiting microbial growth (e.g., phenylmercuric nitrate, thimerosal, benzalkonium chloride, phenol, cresol, benzyl alcohol, etc.). Preferably, the method for treating tauopathy by using the composition for treatment of the present disclosure includes administering the composition for treatment of the present disclosure at a pharmaceutically effective amount. The pharmaceutical effective amount may be easily determined by a person skilled in the art according to factors well known in the medical art, including the type of disease, age, body weight, health, and sex of a subject (patient), drug sensitivity of a subject (patient), route of administration, method of administration, number of times of administration, period of treatment, mixing, drug(s) used in combination.

Another aspect of the present disclosure relates to a method for treatment of a disease (e.g., Alzheimer's disease) caused by tau protein accumulation, aggregation, or tangle, the method including directly transplanting, to a site of lesion, a composition containing brain cells having Foxa2 and Nurr1 or Nurr1 introduced thereinto in a therapeutically effective amount. The transplantation and cell incubation may be carried out by using known methods that are widely known to a person skilled in the art.

The term "therapeutically effective amount" of the cells refers to an amount sufficient to stop or relieve a physiological effect of a subject or patient, caused by tauopathy. The therapeutically effective amount of the cells used may depend on the needs of a subject (patient), age, physiological condition, and health of a subject (patient), a predetermined therapeutic effect, the size and area of tissue in need of treatment, the severity of lesion, and a selected delivery route. In addition, a low cellular dose of the cells may be administered to one or more sites in a predetermine target tissue in the form of small multiple grafts. The cells of the present disclosure may be completely isolated before transplantation, for example, to form a suspension of single cells, or may be almost completely isolated before transplantation, for example, to form small cell aggregates. The cells may be administered by transplanting or moving such a suspension or small cell aggregates to a predetermined tissue site and reconstructing or regenerating a functionally deficient region.

A suitable dose range of the cells to be administered to achieve therapeutic effectiveness may be properly used for or a subject or a patient, within the ordinary skill of a person skilled in the art. For example, the dose range of the cells may be in a range of approximately 1,000 to 1,000,000,000 or more, but not effective for a low dose, and may not exclude the possibility of side actions for a high dose, and therefore, 100,000 to 50,000,000 may be preferable.

However, the dose of the cells may be properly finally determined by a physician's judgment in consideration of the type of formulation, the administration method, age or weight of a subject (patient), symptoms of a patient, and the like, but the present disclosure is not limited thereto.

The appropriate dose of the composition of the present disclosure varies depending on factors, such as the formulating method, manner of administration, age, body weight, or sex of a subject (patient), severity of disease, food, time of administration, route of administration, excretion rate, and response sensitivity, and the ordinarily skilled doctor can easily judge and prescribe the dose effective for desired treatment. Generally, the pharmaceutical composition of the present disclosure contains $1\times10^3$ to $1\times10^{13}$ vg/µl of a viral vector or a viral gene, and may be typically injected at a dose of $1\times10^6$ to $3\times10^{15}$ vg/dose of a viral vector or a viral gene once to five times, and for sustained effects, the injection may be again conducted by a similar method after several months or several years.

In the present disclosure, the composition may be used in the form of the above-described medicine preparation.

In the present disclosure, the "gene therapeutic agent" refers to a medicine wherein a gene material or a carrier carrying a gene material is administered to the human body for the purpose of disease treatment or the like.

For the composition of the present disclosure which is applicable as a gene therapeutic agent, a pharmaceutically acceptable carrier is sterile and biocompatible. Therefore, one or more of saline, sterile water, a Ringer's solution, buffered saline, an albumin injection solution, a dextrose solution, a maltodextrin solution, glycerol, ethanol, and a combination thereof may be used, and as needed, the other typical additives, such as an antioxidant, a buffer, and a bacteriostatic agent, may be added. Also, a diluent, a dispersant, a surfactant, a binder, and a lubricant are additionally added to the composition, which may be then formulated into an injectable formulation, such as an aqueous solution, a suspension, or an emulsion, a pill, a capsule, or a tablet. In addition, target organ-specific antibodies or other ligands may bind with the carrier so that the carrier can act in a target organ-specific manner.

The above-described contents may be applied or correspond to the composition, except that a vector expressing Nurr1 and Foxa2 or Nurr1 is directly used instead of brain cells expressing Nurr1 and Foxa2 or Nurr1.

Furthermore, the present disclosure provides a method for prevention or treatment of tauopathy, the method including administering to a subject the composition containing brain cells having been transformed with Nurr1 and Foxa2, or only Nurr1, at a therapeutically effective amount.

Features and advantages of the present disclosure are summarized as follows.

(a) The present disclosure provides a composition for inhibiting tau protein accumulation, aggregation, or tangle, the composition comprising a vector carrying Nurr1 and Foxa2 genes or a Nurr1 gene.

(b) The present disclosure provides a composition for inhibiting tau protein accumulation, aggregation or tangle, the composition comprising neurons or glia having Nurr1 and Foxa2 genes or a Nurr1 gene introduced thereinto.

(c) The present disclosure provides a composition for inhibiting tau protein phosphorylation, the composition comprising a vector carrying Nurr1 and Foxa2 genes or a Nurr1 gene.

(d) The present disclosure provides a composition for inhibiting tau protein phosphorylation, the composition comprising neurons or glia having Nurr1 and Foxa2 genes or a Nurr1 gene introduced thereinto.

(e) The present disclosure provides a composition for prevention or treatment of a disease caused by tau protein accumulation, aggregation, or tangle, the composition comprising a vector carrying Nurr1 and Foxa2 genes or a Nurr1 gene.

(f) The present disclosure provides a composition for prevention or treatment of a disease caused by tau protein accumulation, aggregation, or tangle, the composition comprising neurons or glia having Nurr1 and Foxa2 genes or a Nurr1 gene introduced thereinto.

(g) The present disclosure provides a pharmaceutical composition for prevention or treatment of tauopathy, the composition comprising a vector carrying Nurr1 and Foxa2 genes or a Nurr1 gene.

(h) The present disclosure provides a pharmaceutical composition for prevention or treatment of tauopathy, the composition comprising neurons or glia having Nurr1 and Foxa2 genes or a Nurr1 gene introduced thereinto.

(i) The inhibitor and composition of the present disclosure, when used, can be utilized in the prevention or treatment of a cerebral nervous disease, such as Alzheimer's disease, caused by tau protein accumulation, aggregation, or tangle.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Figure 1:
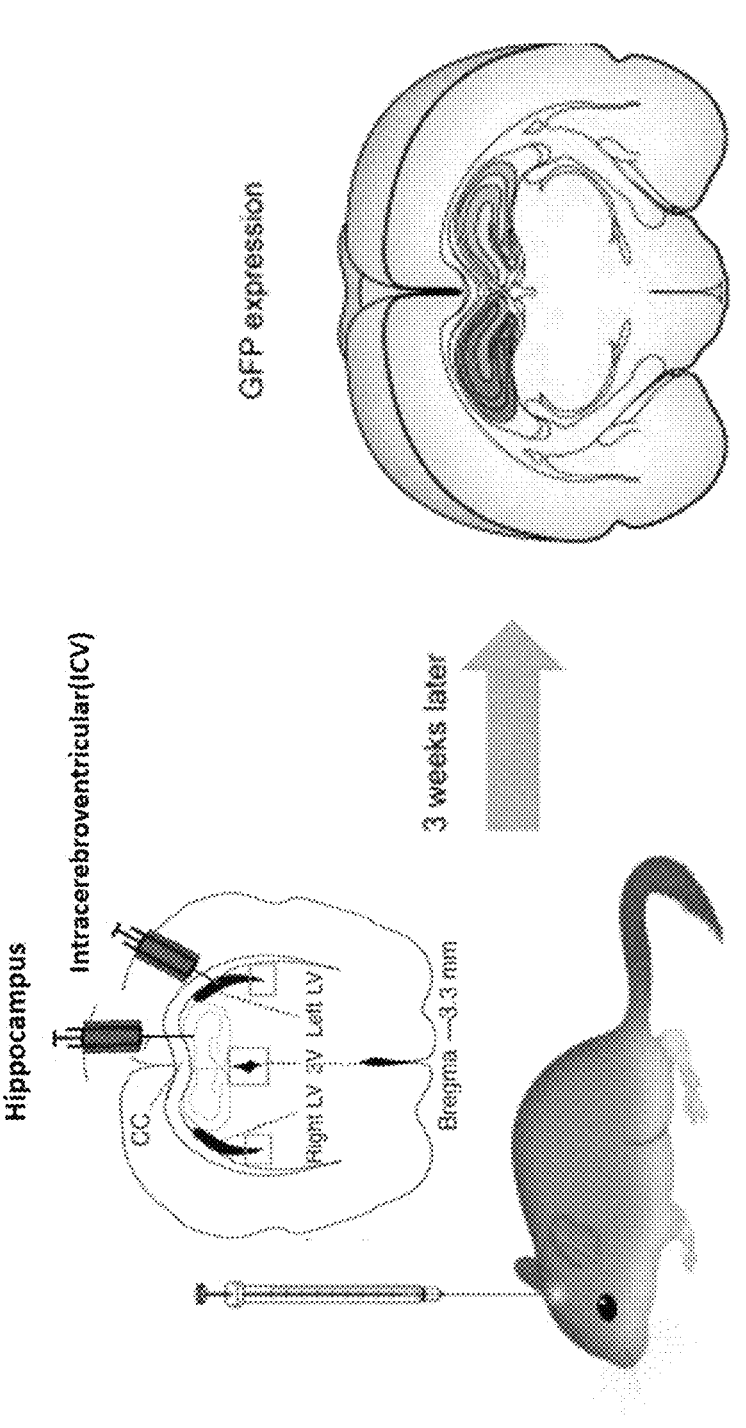
FIG. 1 shows a gene delivery system test procedure using AAV9 virus.

Hereinafter, the present disclosure will be described in more detail with reference to examples. These examples are only for illustrating the present disclosure more specifically, and it would be apparent to those skilled in the art that the scope of the present disclosure is not limited by these examples according to the gist of the present disclosure.

The terms used herein are defined as follows.

The term "brain cells" refers to cells disposed in the brain, and the brain cells are composed of neurons (neuron cells), glia (glial cells), and the like.

The term "neuron" refers to cells from the central system, and the terms "neuron" and "neuronal cell" may be interchangeably used herein.

The term "glial cells" refers to cells that occupy the largest part of cells present in the brain, and the glial cells include astrocytes or microglial cells.

The astrocytes are involved in the protection and nutrition supply of neurons and inflammation, and the microglial cells are cells responsible for inflammation in the brain and are known as a group of cells that play an important role in brain diseases, such as Alzheimer's disease.

The term "transduction" refers to a process in which a genetic trait is transferred from one cell to another cell by means of a bacteriophage. When any type of bacteria is infected with a bacteriophage, phage DNA binds to host DNA. When the phages are released through cell lysis, bacteriophages holding some of the host DNA rather than some of their own DNA are often released from bacterial cells. When other bacteria are infected with such phages, a gene of the previous host is newly introduced into the bacteria so that the bacteria can have a new trait. The term "transduction" in biologic research generally refers to a process in which a specific exogenous gene is introduced and expressed in target cells using a viral vector.

The term "inhibiting accumulation, aggregation, or tangle" has concepts encompassing cases where the accumulation, aggregation, or tangle of tau proteins and/or amyloid β is inhibited by preventing the production thereof and cases where the accumulation, aggregation, or tangle of the already produced tau proteins and/or amyloid β is inhibited by degradation.

The "subject" may refer to a vertebrate to be tested for treatment, observation or experiments, preferably a mammal, for example, a cow, a pig, a horse, a goat, a dog, a cat, a rat, a mouse, a rabbit, a guinea pig, a human, or the like.

The term "tissue or cell sample" refers to an assembly of similar cells obtained from tissue of a subject or patient. A source of the tissue or cell sample may be a freshly lyophilized and/or preserved organ or tissue sample or a solid tissue from a biopsy or aspirate; blood or any blood components; or cells at an optional time of pregnancy or development of the target. The tissue sample may be primary or cultured cells or a cell line.

The term "treatment" refers to an approach for obtaining beneficial or preferable clinical results. For the purpose of the present disclosure, the beneficial or preferable clinical results encompass, without limitation, the palliation of a symptom, a decrease in the extent of a disease, the stabilization (that is, no worsening) of a disease condition, a delay of disease progression or a decrease in disease progression rate, (partial or overall) improvement, temporary palliation or a relief of a disease condition, the probability of being either detectable or undetectable, and the like. In addition, the term "treatment" may refer to an increase in survival rate compared with an expected survival rate when a subject receives no treatment. The "treatment" indicates all types of methods, such as therapeutic treatment and prophylactic or preventive measures. The treatments include treatments required for disorders to be prevented and already developed disorders. The term "palliating" a disorder refers to reducing an extent of disease condition and/or an undesirable clinical symptom and/or delaying or lengthening a time course of disease progression, when compared with the untreated disorders.

The term "gene therapeutic agent" refers to a medicine in which a gene material or a carrier carrying a gene material is administered to the human body for the purpose of the treatment of a disease or the like.

The term "cell therapeutic agent" refers to a medicine (according to U.S. FDA regulations) used for the purpose of treatment, diagnosis, and prophylaxis using cells and tissues prepared through isolation from a human, culturing, and special manipulation, that is, a medicine used for the purpose of treatment, diagnosis and prophylaxis through a series of actions of proliferating and selecting living autologous, allogeneic, or xenogeneic cells in vitro to restore the functions of cells or tissues, or changing biological characteristics of cells by another method. Cell therapeutic agents are mainly classified into somatic cell therapeutic agents and stem cell therapeutic agents depending on the differentiation level of cells.

The term "mammal" in need of treatment refers to any animal classified as a mammal, including a human, livestock and farm livestock, and an animal for zoos, sports, or pets, such as a dog, a horse, a cat, cattle, or a monkey. Preferably, the mammal is a human.

The term "administration" refers to an introduction of the composition of the present disclosure into a subject or a patient by using any suitable method. The composition of the present disclosure may be administered through various routes of oral or parenteral administration as long as the composition can reach target tissue. The composition may be administered intraperitoneally, intravenously, intramuscularly, subcutaneously, intradermally, orally, topically, intranasally, intrapulmonarily, and rectally, but the present disclosure is not limited thereto.

Herein, the term "effective amount" refers to a desired amount required to delay or completely interrupt the onset or progression of a certain disease to be treated. In the present disclosure, the composition may be administered at a pharmaceutically effective amount. It would be obvious to a person skilled in the art that a proper amount of the composition used daily is determined by a medical treatment within an accurate medical judgment range.

For the purpose of the present disclosure, a specific therapeutically effective amount for a certain subject or patient is preferably differently applied according to various factors, including the types and extents of reactions to be achieved, the specific composition including whether another preparation is used in accordance with circumstances, the age, weight, general physical condition, sex, and diet of a subject (patient), the time and route of administration, the secretion rate of the composition, the duration of treatment, and drugs co-administered or used at the same time together the specific composition, and similar factors well known in the field of medicine Unless otherwise defined, all of the technical terms used in the present disclosure have the same meanings as commonly understood by a person skilled in the art to which the present disclosure pertains. In addition, preferred methods or samples are disclosed in this specification, and similar or equivalent methods or samples are also included in the scope of the present disclosure. The contents of all publications disclosed as references herein are incorporated herein.

Example 1: Investigation of Tauopathy Treatment Effect and Alleviation of Cognitive Impairment (Learning and Memory) Through Nurr1 and Foxa2 Gene Introduction Materials and Method (1) Animal Care and Experiments All procedures for 3×FAD animal model experiments were approved by the Institutional Animal Care and Use Committee (IACUC) at the Hanyang College of Medicine under the approval number 2018-0047A. In addition, all procedures for 3×FAD animal model experiments were carried out according to the guidelines on the use of experimental animals at Hanyang University. Animals were housed in a specific pathogen-free barrier facility with a 12-hour light/dark cycle and maintained on standard chow (5053 PicoLab® Rodent Diet 20). The sizes of the animals for the present experiments were determined by in-vitro assays and a pilot test of the present experiments without previous statistical calculation. The experiments were performed in accordance with the NIH guideline. To minimize bias, behavioral assays have mostly been assessed by two experimenters in a blinded-experiment fashion. Alzheimer's disease transgenic (3×Tg-AD) mice (Jackson Laboratory, Maine, USA) at 18 and 15 months of age were used in the experiments.

(2) Stereotaxic AAV Injection into Alzheimer's Disease Model Mice

To the Alzheimer's disease transgenic (3×Tg-AD) mice (Jackson Laboratory, Maine, USA) at 18 months (18 m) and 15 months (15 m) of age, viral vectors comprising Nurr1-AAV9 (1 μl)+Foxa2-AAV9 (1 μl) (total 2 μl, $10^{12}$ vg/μl, Nurr1+Foxa2 group), or Nurr1-AAV9 (1 μl)+control AAV9 (1 μl) (total 2 μl, $5\times10^{11}$ vg/μl, Nurr1 alone group), or a control group having AAV9 virus alone (2 μl, $10^{12}$ vg/μl, control group only) was injected into the hippocampus (1.5 mm posterior to the bregma; ±1 mm lateral from the midline; −2 mm ventral to the dura) and the intracerebroventricle (0.9 mm posterior to the bregma; ±1.7 mm lateral from the midline; −2.2 mm ventral to the dura) over 10 minutes under anesthesia induced by Zoletil 50 (0.1 mg/kg) mixed with Rompum (93.28 μg/kg). A needle (26 gauge) was left in the injection site for 5-10 minutes after completion of each injection, and removed slowly. When inaccurate injection at the hippocampal and intracerebroventricular (ICV) sites were confirmed, the mice were excluded from the analysis.

(3) Virus Production

Lentiviral vectors expressing Nurr1 or Foxa2 under the control of a CMV promoter were generated by inserting the respective cDNAs into a multi-cloning site of pCDH (System Biosciences, Mountain View, CA). pGIPZ-shNurr1 and pGIPZ-shFoxa2 lentiviral vectors were purchased from Open Biosystems (Rockford, IL). The empty backbone vectors (pCDH or pGIPZ) were used as negative controls. The lentiviruses were produced and used for transduction of in-vitro cultures as described above (Yi S H, He X B, Rhee Y H, Park C H, Takizawa T, Nakashima K, Lee S H (2014) Foxa2 acts as a co-activator potentiating expression of the Nurr1-induced DA phenotype via epigenetic regulation. Development 141: 761-772). Titers of the lentiviruses were determined using a QuickTiter™ HIV Lentivirus quantification kit (Cell Biolabs, San Diego, CA), and 200 µl/well (a 24-well plate) or 2 ml/6 cm plates with $10^6$ transducing units (TU)/ml (60-70 ng/ml) were used for each transduction reaction. To induce in-vivo expression by stereotaxic injection, AAVs expressing Nurr1 or Foxa2 (tagged with hemagglutinin (HA)) under the control of the CMV promoter were generated by subcloning the respective cDNAs into a pAAV-MCS vector (Addgene, Cambridge, MA). To assess the expression efficiency of a transgene, GFP-expressing AAVs were also generated. Packaging and production of the AAVs (serotype 9 or 2) were performed by the Korea Institute of Science and Technology (Seoul, Korea). AAV titers were determined using a QuickTiter™ AAV quantification kit (Cell Biolabs). Co-expression studies were carried out by infecting cells with mixtures of individual viral preparations (1:1, v:v).

(4) Immunostaining

Cultured cells and cryosectioned brain slices were stained with the following primary antibodies: Nurr1 (1:500, rabbit, embryonic day 20, Santa Cruz Biotechnology, Dallas, TX and 1:1,000, mouse, R&D Systems); Foxa2 (1:500, goat, Santa Cruz Biotechnology); GFP (1:2,000, rabbit, Life Technologies); GFAP (1:200, mouse, MP Biomedicals, Santa Ana, CA); Iba-1 (1:200, rabbit, Wako), NeuN (1:100, mouse, EMD Milipore); TAU (1:500, mouse, Santa Cruz Biotechnology); pTAU (1:500, rabbit, ABcam)

The cultured cells were fixed in 4% paraformaldehyde (PFA) of PBS solution, and blocked by 0.3% Triton X-100 and 1% BSA for 40 minutes. In addition, the cells were cultured together with the primary antibodies overnight at 4° C. Secondary antibodies for visualization were as follows: Cy3 (1:200, Jackson Immunoresearch Laboratories) or Alexa Fluor 488 (1:200, Life Technologies). The stained cells were mounted together with VECTASHIELD and DAPI mounting solution (Vector Laboratories), and images were obtained by an epifluorescence microscope (Leica) and a confocal microscope (Leica PCS SP5).

(5) Behavior Tests (5)-1. Water Maze Method

The Water Maze method is also called the Morris Water Maze, and is widely used in studying spatial memory and learning. Animals are placed in puddles opaquely colored with powdered, non-fat milk or non-toxic paint, where the animals need to swim to a hidden escape platform. Since the animals are in opaque water, the animals cannot see the platform and cannot rely on odors to find escape routes. Instead, the animals need to rely on outer clues or clues outside the maze. As the animals get more used to the work, the animals can find the platform faster. This paradigm, developed by Richard G. Morris in 1984, has become one of the "gold standards" in behavioral neuroscience.

(5)-2. Y-Maze Method

The Y-maze method is widely used to evaluate behavior in preclinical studies to study spatial learning and memory. In the Y maze method, animals were placed at the end of one of the three arms in a Y-shaped maze, where the animals decided whether to move left or right at the crossroads. These tests can be repeated several times for one animal. The observer recorded a series of selections of animals in the Y-maze (e.g., the number of visits to a particular arm, the total number of visits to three arms, the number of times the left arm is selected for animals, the number of times the right arm is selected for animals). The use of the Y maze test encompasses a spontaneous alternation test and a cognitive memory test. In the spontaneous alternation test, the observer observed and recorded whether animals tended to visit an arm that has not recently been visited (e.g., measured the number of spontaneous alternations). These tests have been found to be sensitive to hippocampal injury, genetic manipulation, and memory loss drugs.

(6) Cell Counting and Statistical Analysis

Immunostained and DAPI-stained cells were counted in random areas of each culture coverslip by using an eyepiece grid at a magnification of 200× or 400×. For all figures, data are expressed as the mean±SEM and statistical tests are justified as appropriate. Statistical comparisons were made using Student's t-test (unpaired) or 2-tailed or one-way ANOVA, followed by Bonferroni post hoc analysis using SPSS (Statistics 21; IBM Inc. Bentonville, AR, USA). The n, P-values, and statistical analysis methods are indicated in the figure legends. The P value of less than 0.05 was considered to be significant.

Results (1) Effect of Nurr1 and Foxa2 Gene Introduction on Tauopathy

Since adeno-associated virus (AAV) is very poorly immunogenic in the human body, the AAV9 serotype, which tends to mainly infect neurons and glia in the brain, was used to construct a Nurr1 and Foxa2 gene delivery system specifically targeting glia. For expressing Nurr1 and Foxa2 genes, a CMV or GFAP promoter was employed. Nurr1+Foxa2-AAV9 was into the hippocampus and intracerebroventricle (ICV), which are lesion sites of Alzheimer's disease, a kind of tauopathy.

Figure 2:
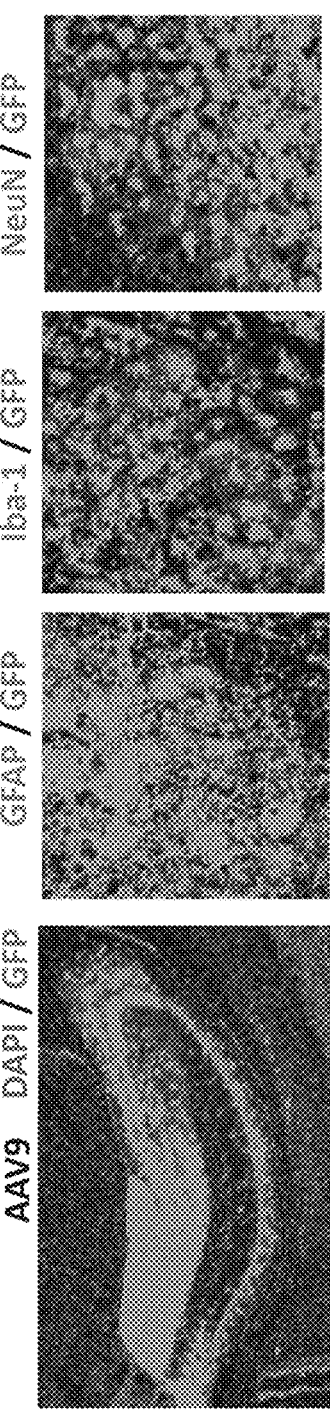
FIG. 2 shows gene delivery test results (GFP expression degrees in hippocampus and intracerebroventricle) using AAV9 virus.

For testing gene delivery using the AAV9 virus, the AAV9 virus that is specific to astrocytes and expresses green fluorescent protein (GFP) under the control of GFAP promoter was injected to both the hippocampus and the intracerebroventricle (ICV) of mice. Three weeks after injection with GFP-AAV9 virus, GFP expression was measured (FIG. 1). As a result of injecting GFP-AAV9 to the hippocampus and the intracerebroventricle (ICV), GFP was expressed across the hippocampus and specifically in GFAP+ astrocytes (FIG. 2). GFAP, NeuN, and Iba1 were used as markers for astrocytes, mature neurons, and microglia, respectively. The co-expression of GFAP and GFP, lack of co-expression of GFP and NeuN, and lack of co-expression of GFP and Iba1 indicated that the virus expressed the genes specifically in astrocytes.

The tau proteins are a group of microtubule-associated proteins (MAP) in axons of normal neuronal cells. When aggregation of tau protein occurs in the brain, it incurs tau-mediated neuronal injury and dysfunction, which are described to be an etiological factor and symptom typical of Alzheimer's disease.

Nurr1 and Foxa2 genes were introduced specifically into hippocampal and intracerebroventricular glial cells of 3×FAD mice at 15 and 18 months of age, which are the Alzheimer's disease animal models having tau proteins aggregated in the brain, similar to human patients. Two months after introduction of the genes, tau proteins were quantitatively analyzed by immunostaining in the hippocampal region.

Figure 3:
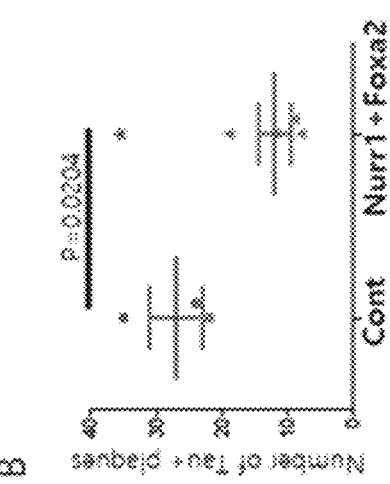
FIG. 3 shows immunostaining results that confirm the fluorescence of beta-amyloid and tau protein in the hippocampus region of the mice in which Nurr1 and Foxa2 genes were introduced into brain cells.
Figure 3:
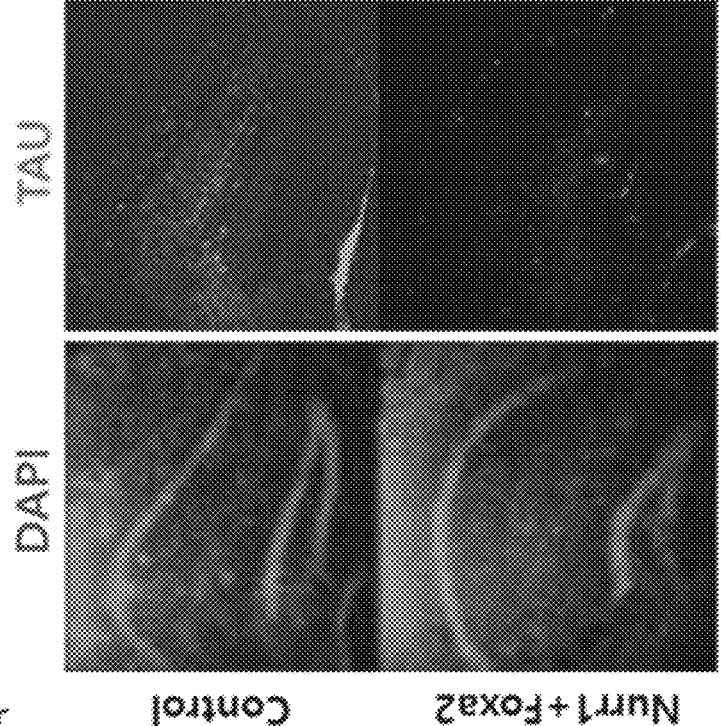

FIG. 3A shows a significant reduction of tau-specific tangles in the hippocampal region of the Nurr1+Foxa2-

AAV9-injected 3×FAD mice, compared to that of the control-AAV9-injected 3×FAD mice. FIG. 3B shows quantitative data of Tau+tangles.

Tau proteins present even in a normal condition, but abnormal tau proteins are known to cause neurodegenerative diseases, and the hyperphosphorylation of tau proteins is a characteristics of normal tau proteins.

Nurr1 and Foxa2 genes were introduced specifically into hippocampal and intracerebroventricular glial cells of 3×FAD mice at 15 and 18 months of age. Two months after introduction of the genes, phosphorylated tau proteins (phosphor-tau, pTau) were quantitatively analyzed by immunostaining in the hippocampal region.

Figure 4:
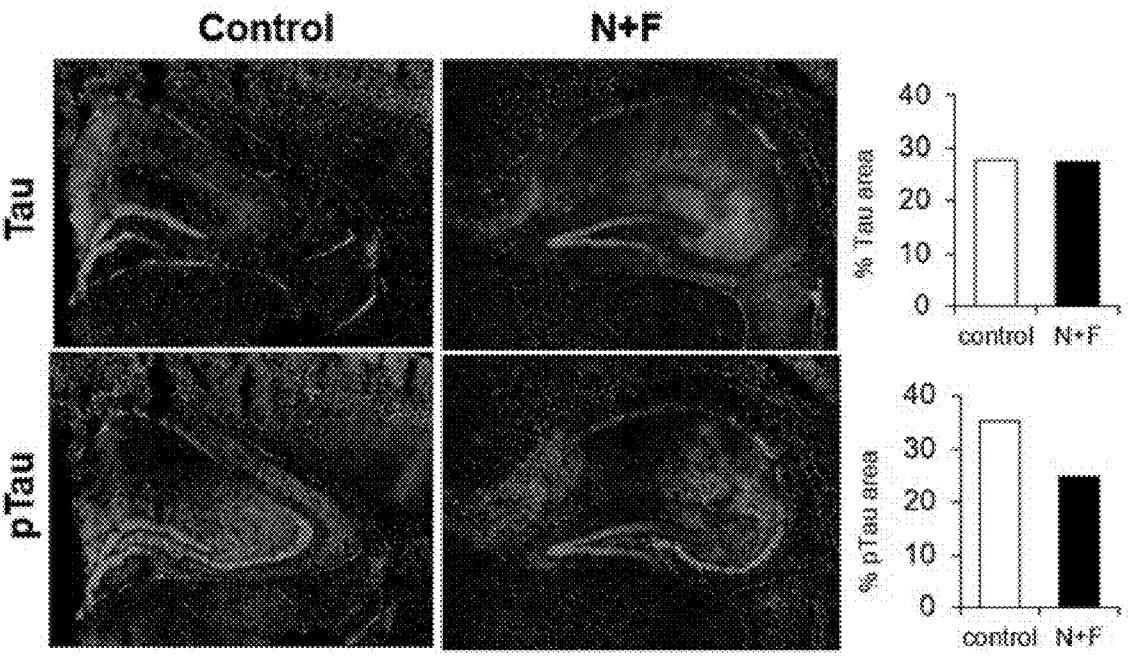
FIG. 4 shows immunostaining results that confirm the fluorescence of tau protein and phosphorylated tau (phosphor-tau, pTau) protein in the hippocampus region of the mice in which Nurr1 and Foxa2 genes were introduced into brain cells.
Figure 5:
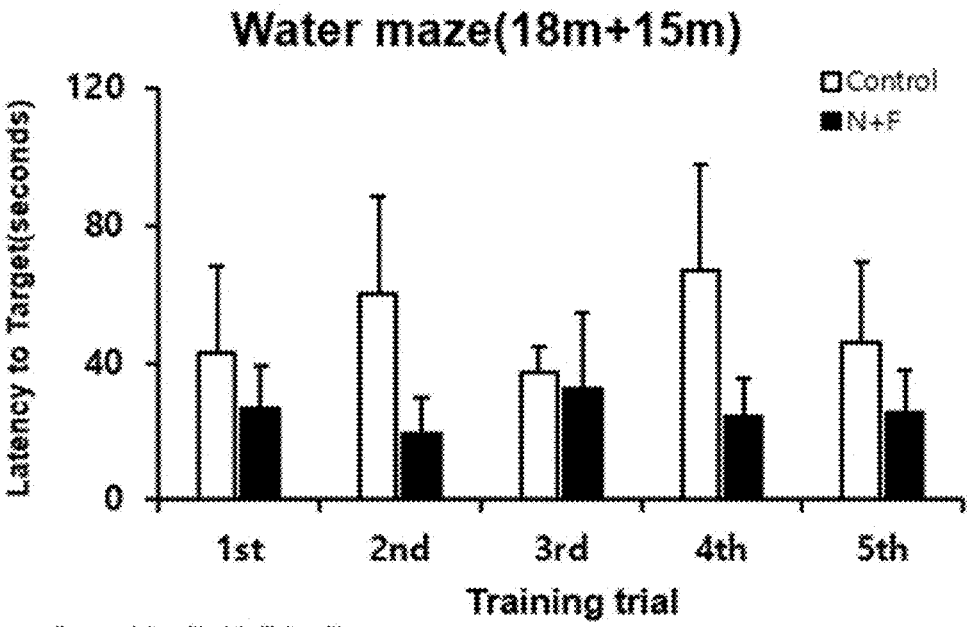
FIG. 5 shows Water Maze test results that compare the behavioral indicator of the mice into which the Nurr1- and Foxa2-AAV9 virus was injected and the behavioral indicator of the mice into which the control virus (GFP-AAV9) was injected.
Figure 6:
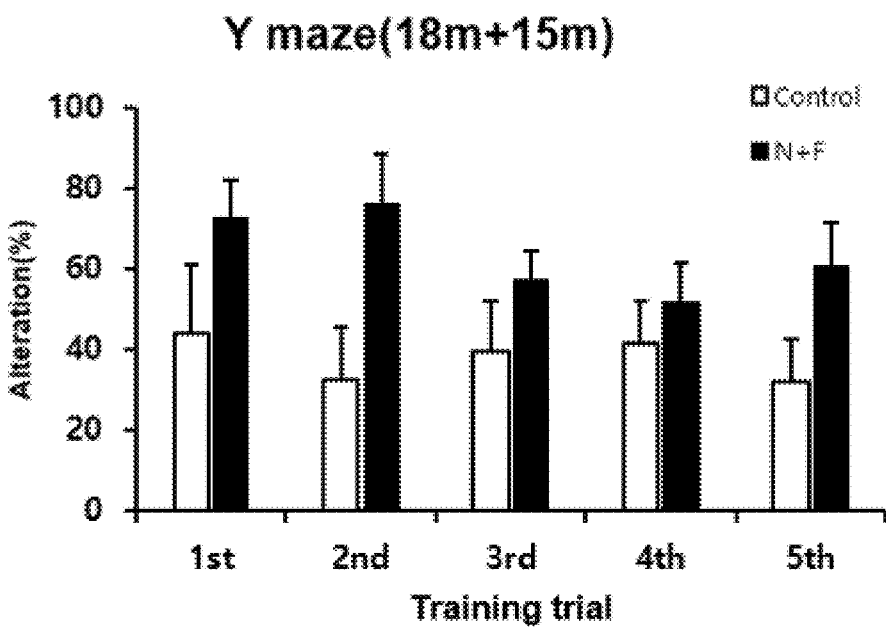
FIG. 6 shows Y Maze test results that compare the behavioral indicator of the mice into which the Nurr1- and Foxa2-AAV9 virus was injected and the behavioral indicator of the mice into which the control virus (GFP-AAV9) was injected.
Figure 7:
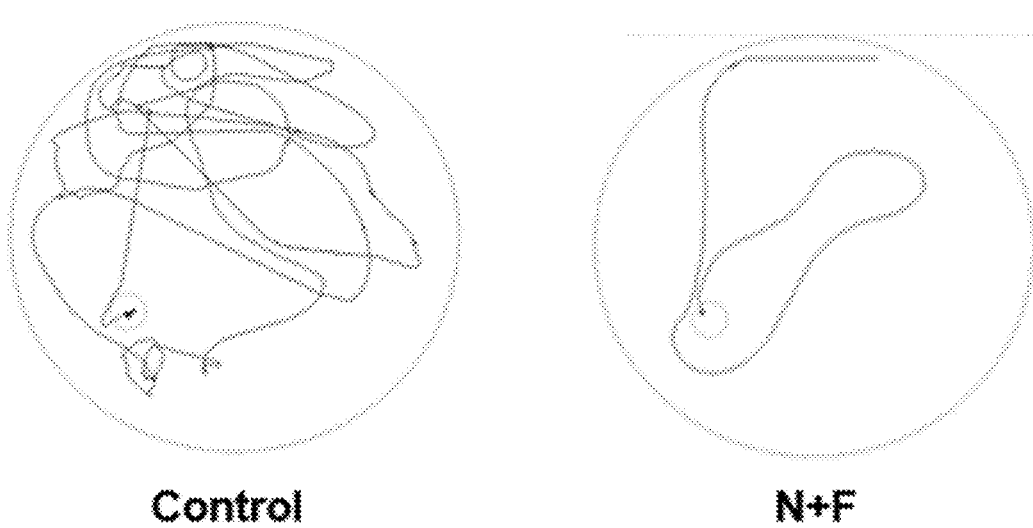
FIG. 7 shows Water Maze test results that compare the behavioral indicator (movement pattern being recorded) of the mice into which the Nurr1- and Foxa2-AAV9 virus was injected and the behavioral indicator of the mice into which the control virus (GFP-AAV9) was injected.
Figure 8:
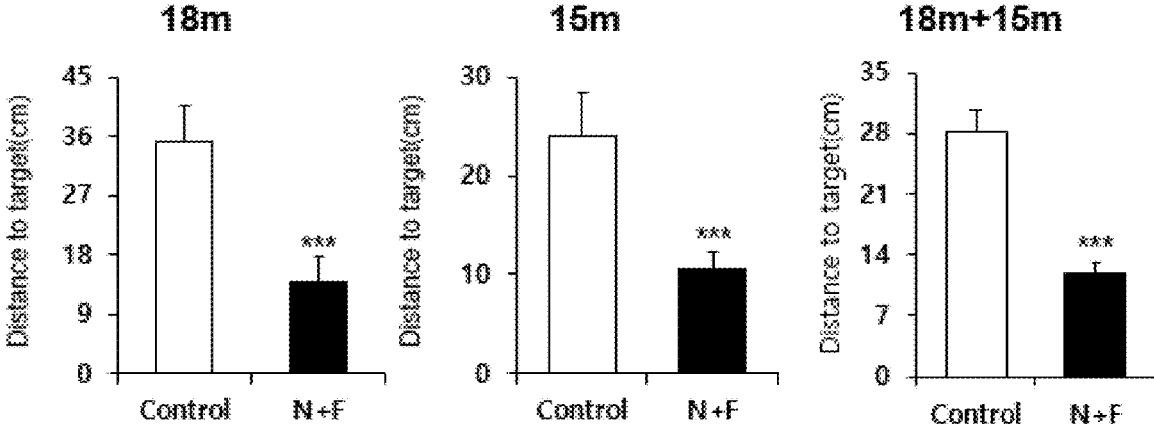
FIG. 8 shows Water Maze test results that compare the behavioral indicator (distance to target) of the mice into which the Nurr1- and Foxa2-AAV9 virus was injected and the behavioral indicator of the mice into which the control virus (GFP-AAV9) was injected.
Figure 9:
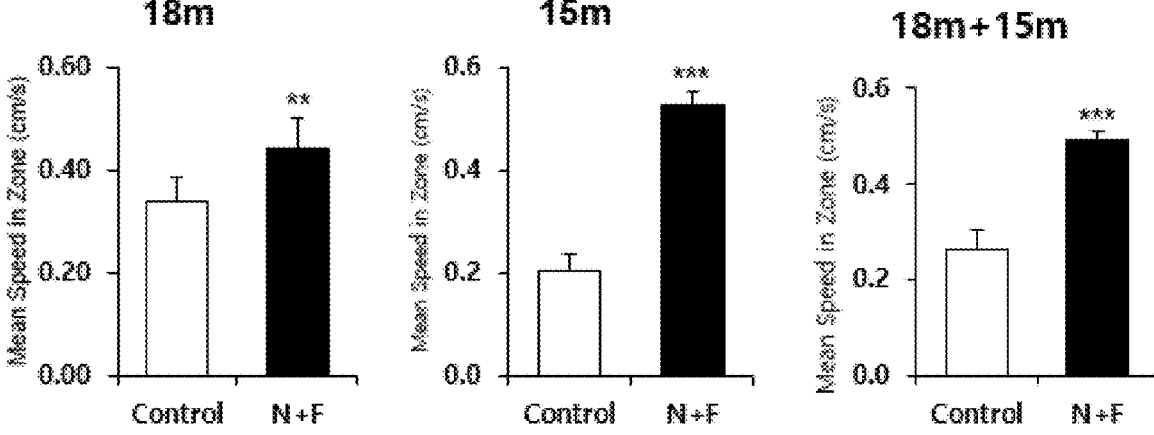
FIG. 9 shows Water Maze test results that compare the behavioral indicator (mean speed) of the mice into which the Nurr1- and Foxa2-AAV9 virus was injected and the behavioral indicator of the mice into which the control virus (GFP-AAV9) was injected.

As a result, AAV9-pGFAP-Nurr1+Foxa2-injected 3×FAD mice were found to have reduced phosphorylated tau levels compared with the control AAV9-injected mice, as measured by immunohistochemistry (IHC) (FIG. 4).

The result indicates that overexpression of Nurr1 and Foxa2 can reduce the absolute quantity of tau tangles formed or the amount of phosphorylated tau protein, suggesting the therapeutic effect of the overexpression of Nurr1 and Foxa2 on tau pathology.

(2) Alleviation of Cognitive Impairment (Learning and Memory) by Nurr1 and Foxa2 Gene Delivery in Alzheimer's Disease (AD) Mouse Model as Analyzed by Water Maze and Y Maze Behavior Tests Investigation was made to see the effect of glial Nurr1 and Foxa2 expression on the treatment of Alzheimer's disease, a kind of tauopathy. In this regard, Nurr1 and Foxa2 were expressed specifically in hippocampal and intracerebroventricular glial cells of 3×FAD mice at 15-18 months of age, which had undergone the onset of Alzheimer's disease by mutagenesis in the three genes APP, PS1, and tau. Mice at 15-18 months of age were considerably old when account is taken of the fact that mice live about 24 months on average. Three months after delivery of Nurr1 and Foxa2 genes to Alzheimer's disease model mice, the mice were analyzed for cognitive ability.

Alzheimer's disease, which is a kind of tauopathy, is a neurodegenerative disease characterized by slow progression of the impairment of memory and cognitive ability. Water Maze and Y Maze tests were carried out as animal tests for Alzheimer's disease. Both Water Maze and Y Maze tests are authorized experimental methods representative of efficacy experiments for memory and cognitive ability and are used as indicators of behavioral tests for determining the progression of Alzheimer's disease and therapeutic effects on Alzheimer's disease.

About two weeks after injection of Nurr1+Foxa2-AAV9 virus into mice at 15-18 months of age, Water Maze and Y Maze behavioral tests were carried out bi-weekly for two months. Behavioral indices were compared between mice injected with Nurr1+Foxa2-AAV9 virus and control virus (GFP-AAV9). As a result of the behavioral test in the animal models, the Nurr1+Foxa2-expressed mice exhibited better behavioral indices and faster response speeds, compared with the control mice, indicating that glial expression of Nurr1 and Foxa2 brought about a significant improvement in cognitive activity responsible for learning and memory and thus a therapeutic effect on Alzheimer's disease, a kind of tauopathy. That is, the expression of Nurr1 and Foxa2 in brain cells was identified to have a clinical gene therapy effect on Alzheimer's disease (FIGS. 5, 7, 7, 8, and 9).

Example 2: Investigation of p-Tau Protein (Phosphorylated Tau Protein) Formation Inhibition Through Nurr1 and Foxa2 Gene Introduction It was further investigated if the formation of phosphorylated tau protein can be inhibited through Nurr1 and Foxa2 gene introduction.

To Alzheimer's disease transgenic (3×Tg-AD) mice (Jackson Laboratory, Maine, USA) at 18 and 15 months of age with mutation inductions of APP, PS1, and tau, Nurr1-AAV9 (1 μl)+Foxa2-AAV9 (1 μl) (total 2 μl, $10^{12}$ vg/μl, Nurr1+Foxa2 group), Nurr1-AAV9 (1 μl) alone, or saline solution (PBS) were administered into the hippocampus and the intracerebroventricle of the anesthetized mice through stereotaxic micro-injection. Two months after the administration, Alzheimer's disease transgenic mice were sacrificed, fixed in paraformaldehyde (PFA), and then blocked for 1 hour by addition of 0.6% Triton X-100 to 1% BSA/PBS solution. Thereafter, the primary antibodies (p-tau, Tuj1) were bound to the same solution and subjected to tissue staining overnight at 4° C. Secondary staining was carried out by, as second antibodies for visualization, Cy3 (1:200, Jackson Immunoresearch Laboratories), Alexa Fluor 488 (1:200, Life Technologies). The stained cells were mounted together with VECTASHIELD, DAPI mounting solution (Vector Laboratories), and the entorhinal cortex region was taken through a confocal microscope (Leica PCS SP5). The taken images are shown in FIG. 10, and the quantified results thereof are shown in FIG. 11 and Table 1.

TABLE 1

| | PBS administration control group | Nurr1 alone administration group | Nurr1 + Foxa2 administration group |
|---|---|---|---|
| Number of Tuj1/p-tau co-expressed cells | 252 | 141 | 64 |

Figure 10:
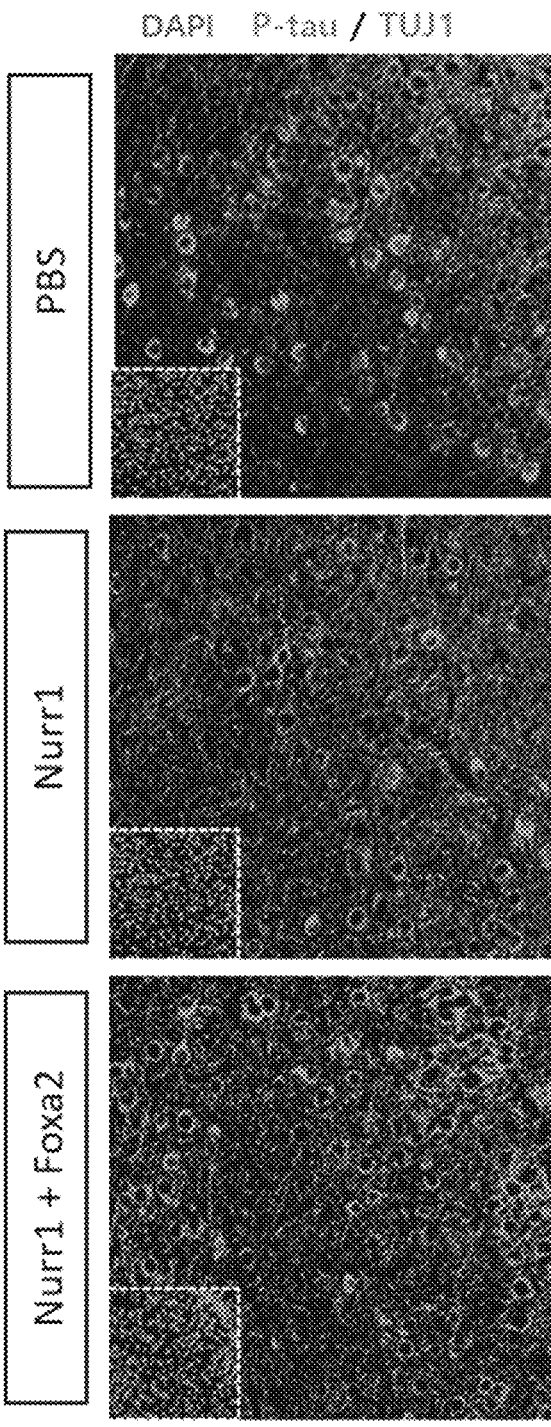
FIG. 10 shows images depicting the results of immunostaining using phosphorylated tau protein (p-tau) and Tuj1 in the PBS administration control group, the Nurr1 alone administration group, or the Nurr1 and Foxa2 co-administration group in the 3×FAD transgenic (Tg) mice.
Figure 11:
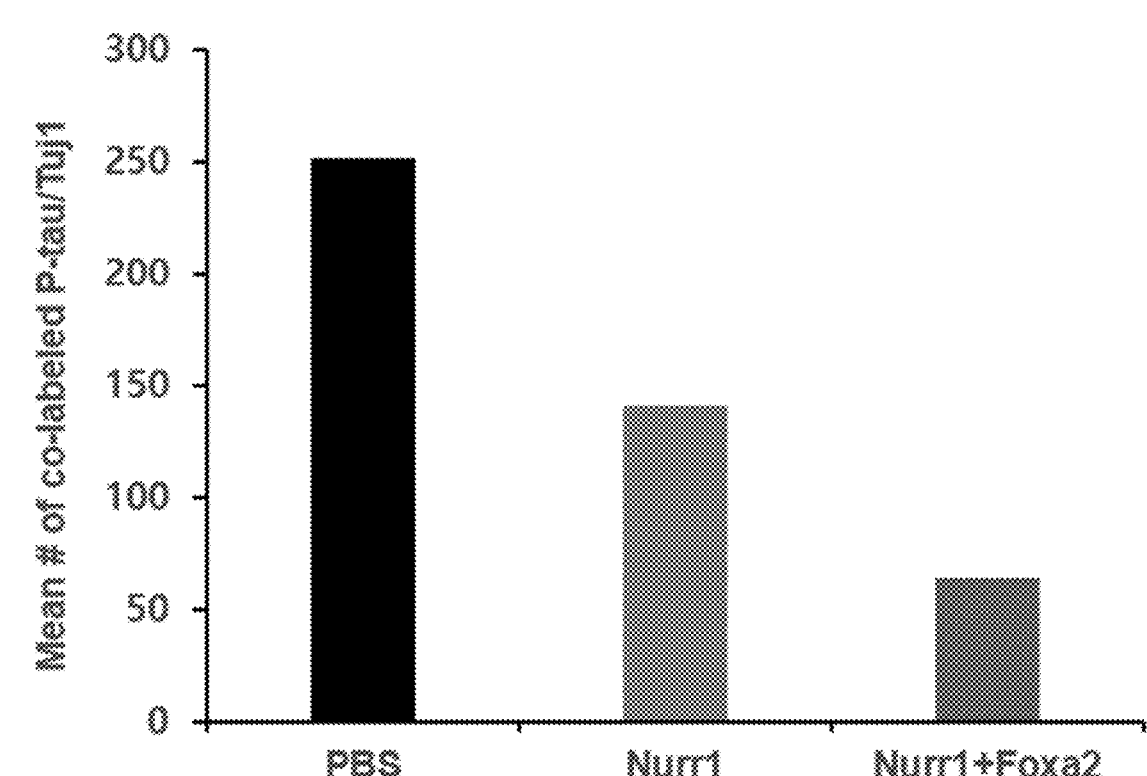
FIG. 11 is a graph depicting the results of immunostaining using phosphorylated tau protein (p-tau) and Tuj1 in the PBS administration control group, the Nurr1 alone administration group, or the Nurr1 and Foxa2 co-administration group in the 3×FAD Tg mice.

As confirmed in FIGS. 10 and 11, the test results verified that the level of the phosphorylated tau protein expressed in the brain neurons of the 3×FAD Tg mice was significantly reduced when Nurr1 and Foxa2 were introduced and expressed, and was significantly reduced when Nurr1 alone was introduced and expressed.

The test results showed that when the transcription factors Nurr1 and Foxa2 were expressed together or Nurr1 was expressed alone in the 3×FAD Tg mice as Alzheimer's disease model mice, the phosphorylated tau protein in neurons was reduced compared with the control group. Considering that the phosphorylated tau protein is a substance constituting neurofibrillary tangles, a major characteristic of Alzheimer's disease, and is accumulated in neurons to cause cell death of neurons, eventually resulting in memory failure, the introduction of Nurr1 and Foxa2 jointly or Nurr1 alone according to the present disclosure is expected to be used in the treatment of tauopathy and Alzheimer's disease.

What is claimed is:

1. A method for inhibiting tau protein accumulation, aggregation, or tangle in a tau-positive subject, the method comprising the steps of:

identifying a subject in need of treatment for inhibiting tau protein accumulation, aggregation tangle, or phosphorylation by confirming the subject as tau-positive; and administering to the subject a therapeutically effective amount of a composition comprising Nurr1 and Foxa2 genes, wherein the composition is injected into the hippocampus and/or the ventricle;

wherein the composition comprises adeno-associated virus (AAV) vectors carrying the Nurr1 and Foxa2 genes; and wherein the AAV serotype is AAV9, wherein the administration of the composition alleviates cognitive impairment in the subject, wherein the alleviation of the cognitive impairment comprises at least one of:

(i) improved behavioral indices and faster response speeds;

(ii) improved cognitive activity responsible for learning and memory; and (iii) reduced tau phosphorylation, thereby resulting in improved cognitive function.

2. The method of claim 1, wherein the composition is injected into the hippocampus using a stereotaxic system comprising a stereotaxic micro-injection.

3. The method of claim 1, wherein the composition is injected into the ventricle using an intraventricular injection.

4. The method of claim 1, wherein the composition comprises $1\times10^3$ to $1\times10^{13}$ vg/µl of the viral vectors.

5. The method of claim 1, wherein the composition is injected at a dose of $1\times10^6$ to $3\times10^{15}$ vg/µl of the viral vectors once to five times.

6. The method of claim 1, wherein the composition comprises adeno-associated virus (AAV) vectors carrying nucleotide sequences of the Nurrl and Foxa2 genes that encode functional equivalents of NURR1 and FOXA2 protein.

7. The method of claim 1, wherein the composition is prepared as a single-dose ampoule or as a multi-dose container.

8. The method of claim 1, wherein the composition is administered together with a pharmaceutically acceptable carrier.

9. The method of claim 1, wherein the composition is sterile and biocompatible.

10. A method for treatment of a disease in a tau-positive subject caused by tau protein accumulation, aggregation, or tangle, the method comprising the steps of:

identifying a subject in need of treatment of a disease caused by tau protein accumulation, aggregation tangle, or phosphorylation by confirming the subject as tau-positive; and administering to the subject a therapeutically effective amount of a composition comprising Nurrl and Foxa2 genes, wherein the composition is injected into the hippocampus and/or the ventricle;

wherein the composition comprises adeno-associated virus (AAV) vectors carrying the Nurr1 and Foxa2 genes; and wherein the AAV serotype is AAV9, wherein the administration of the composition alleviates cognitive impairment in the subject, wherein the alleviation of the cognitive impairment comprises at least one of:

(i) improved behavioral indices and faster response speeds;

(ii) improved cognitive activity responsible for learning and memory; and (iii) reduced tau phosphorylation, thereby resulting in improved cognitive function.

11. The method of claim 10, wherein the composition is injected into the hippocampus using a stereotaxic system comprising a stereotaxic micro-injection.

12. The method of claim 10, wherein the composition is injected into the ventricle using an intraventricular injection.

13. The method of claim 10, wherein the composition comprises $1\times10^3$ to $1\times10^{13}$ vg/µl of the viral vectors.

14. The method of claim 10, wherein the composition is injected at a dose of $1\times10^6$ to $3\times10^{15}$ vg/µl of the viral vectors once to five times.

15. The method of claim 10, wherein the composition comprises adeno-associated virus (AAV) vectors carrying nucleotide sequences of the Nurrl and Foxa2 genes that encode functional equivalents of NURR1 and FOXA2 protein.

16. The method of claim 10, wherein the composition is prepared as a single-dose ampoule or as a multi-dose container.

17. The method of claim 10, wherein the composition is administered together with a pharmaceutically acceptable carrier.

18. The method of claim 10, wherein the composition is sterile and biocompatible.

\* \* \* \* \*